(12) United States Patent
Lin et al.

(10) Patent No.: US 7,514,587 B1
(45) Date of Patent: Apr. 7, 2009

(54) SELECTIVE REDUCTION OF GLYCEROL BY POROUS SILICON

(75) Inventors: Victor Shang-Yi Lin, Ames, IA (US); Hung-Ting Chen, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 12/152,344

(22) Filed: May 14, 2008

Related U.S. Application Data

(60) Provisional application No. 60/930,216, filed on May 15, 2007.

(51) Int. Cl.
*C07C 29/132* (2006.01)
(52) U.S. Cl. .................................................. 568/861
(58) Field of Classification Search .................. 568/861
See application file for complete search history.

(56) References Cited

FOREIGN PATENT DOCUMENTS

WO   WO-9905085 A1   2/1999
WO   WO-03035582 A1   5/2003

OTHER PUBLICATIONS

Kraus, G. A., et al., "Conversion of Lactones into Ethers", *J. Org. Chem.*, 46, (1981),2417-2419.

Kursanov, D. N., et al., "Applications of Ionic Hydrogenation to Organic Synthesis", *Synthesis*, (Sep. 1974),633-651.

Schlaf, M., et al., "Metal-Catalyzed Selective Deoxygenation of Diols to Alcohols", *Angew. Chem. Int. Ed.*, 40(20), (2001),3887-3890.

Wang, K., et al., "Conversion of Glycerol to 1,3-Propanediol via Selective Dehydroxylation", *Ind. Eng. Chem. Res.*, 42, (2003),2913-2923.

Zeng, A.-P., et al., "Bulk Chemicals from Biotechnology: The Case of 1,3-Propanediol Production and the New Trends", *Advances in Biochemcial Engineering/Biotechnology*, vol. 74, (2002),239-259.

Zeng, A.-P., et al., "Chapter 14—Microbial Conversion of Glycerol to 1,3-Propanediol; Recent Progress", *In: ACS Symposium Series 666—Fuels and Chemicals from Biomass*, Saha, B. C., et al., Editors,(1997),264-279.

*Primary Examiner*—Elvis O Price
(74) *Attorney, Agent, or Firm*—Schwegman, Lundberg & Woessner, P.A.; Michael Haukaas

(57) ABSTRACT

The invention provides a method to prepare 1,3-propanediol from glycerol. The glycerol is contacted with porous silicon in the presence of an acid to provide the resulting 1,3-propanediol. The porous silicon can have at least one of three types of silicon hydride moieties of the formula Si—$H_x$, wherein x is 1, 2 or 3. The pores of the porous silicon can be about 1 nm in diameter to about 1 micrometer, and the surface area of the porous silicon can be about 200 to about 800 $m^2/g$.

15 Claims, 2 Drawing Sheets

SELECTIVE REDUCTION OF GLYCEROL BY POROUS SILICON

RELATED APPLICATIONS

This application claims priority under 35 U.S.C. §119(e) to U.S. Provisional Patent Application No. 60/930,216, filed May 15, 2007, which is incorporated herein by reference.

BACKGROUND OF THE INVENTION

For every gallon of biodiesel produced, one pound of glycerin also obtained as a side-product. Biodiesel production is expected to produce an additional one billion pounds of glycerin per year due to the expanding number of plants. Also, about 557 million pounds of glycerin was produced from non-biodiesel sources in 2003. Although there are currently some markets for glycerin, there is mounting concern that glycerin prices may plummet to 5-10 cents per pound or less if future production exceeds demand. Developing a system to make high value chemicals from the glycerin stream will add value for biodiesel producers and maintain a reasonable glycerin price.

The diol, 1,3-propandiol ("PDO"), is currently produced mainly from fossil-based resources by costly chemical processes. The market for PDO is currently about 100 million pounds per year and is growing very rapidly. PDO can be used to prepare new classes of polymers with enhanced functionality. For example, both DuPont and Shell Chemicals have announced plans to commercialize a new polyester, polytrimethylene terephthalate (PTT), wherein PDO has been substituted for ethylene glycol in polyesters. 1,3-Propanediol is a key component of PTT fibers. These fibers display outstanding mechanical and chemical resistance, which are the best characteristics of nylon and polyester.

For example, 1,3-propandiol is a valuable monomer used in industrial polymer syntheses. Traditionally, reduction of polyols can be achieved by either homogeneous hydride reagents or by enzymes. Hydrides, such as lithium aluminum hydride or sodium borohydride, can be explosive and are typically sensitive to moisture. Also, selective reduction of polyols can require multiple protection and deprotection steps due to the presence of multiple hydroxyl groups. These transformations extend and complicate the synthetic procedure. Moreover, each selective protection and deprotection step on a polyol is a challenging task. On the other hand, even through enzymes in general provide high selectivity for chemical reactions, producing large quantities of the target product requires specialized reactors, laborious processes, and specialized enzymes.

Other methods to produce PDO involve fermentation (see Bock et al. "Bioconversion of Glycerine to 1,3-Propanediol as Alternative Use of a By-Product." *Freiberger Forschungshefte A* 2002, *A*866, 125-132; Zeng and Biebl; "Bulk Chemicals From Biotechnology The Case of 1,3-Propane-Diol Production and the New Trends"; Biochemical Engineering Division, GBF—German Research Centre for Biotechnology, Braunschweig, Germany. *Advances in Biochemical Engineering/Biotechnology* 2002, 74 (Tools and Applications of Biochemical Engineering Science), 239-259; Zeng et al. "Microbial Conversion of Glycerol to 1,3-Propanediol: Recent Progress"; *ACS Symposium Series* 1997, 666 (*Fuels and Chemicals from Biomass*), 264-279; and Wang et al.; "Conversion of Glycerol to 1,3-Propanediol via Selective Dehydroxylation" *Industrial & Engineering Chem. Res.* (2003), 42(13), 2913-2923), hydrogenolysis (WO 99/05085 (Drent et al.; "Hydrogenolysis of Gycerol")), and hydrogenation (Schlaf et al., "Metal-Catalyzed Selective Deoxygenation of Diols to Alcohols"; *Angew. Chemie,* 2001, 40, 3887-3890)). The hydrogenation method of Schlaf generated both PDO and 1-propanol. Dennis Miller and coworkers (WO 03/035582 (Werpy et al.; "Hydrogenolysis of 6-Carbon Sugars and Other Organic Compounds")) have evaluated the conversion of glucose and glycerin into 1,2-propanediol. Their high temperature organometallic methodology uses hydrogen gas as the hydrogen atom source. Each of these methods have significant drawbacks, including high costs, cumbersome nature, inefficiency, and the use of various toxic processes and reagents.

Accordingly, there is a need for alternative methods to prepare 1,3-propanediol. These alternative methods would preferably be environmentally friendly, economical, efficient, and easy to perform. The development of new, cost-competitive processes that utilize renewable feedstocks to produce PDO would be an important advance. Introduction of such processes would avoid the use of petroleum, provide substantial energy savings (10 to 19 trillion BTU), and afford a significant market for the bio-products industry.

SUMMARY

The invention provides a method to prepare 1,3-propanediol comprising contacting glycerol with porous silicon in the presence of an acid, wherein the porous silicon contains silicon hydride moieties. The porous silicon can include at least one of three types of silicon hydride moieties, wherein the silicon hydride moieties comprise Si—$H_x$, wherein x is 1, 2 or 3. Typically, the porous silicon will include a combination of the three types of silicon hydride (Si—$H_x$) moieties. The porous silicon can have a surface area of about 200 to about 800 $m^2/g$, about 400 to about 600 $m^2/g$, or about 500 $m^2/g$.

The pores of the porous silicon can have radii of about 1 nm to about 1 μm. In some embodiments, the pores of the porous silicon can have radii of about 1 nm to about 20 nm. In other embodiments, the pores of the porous silicon can have radii of about 10 nm to about 1000 nm. In yet other embodiments, the pores of the porous silicon can have average diameters of about 10 nm, about 20 nm, about 50 nm, about 100 nm, about 250 nm, or about 500 nm.

The glycerol and the porous silicon can be contacted in the presence of a solvent. The solvent can be an organic solvent, such as a chlorinated organic solvent. The chlorinated organic solvent can be, for example, chloroform, dichloroethane, methylene chloride, or a combination thereof. Alternatively, the glycerol and the porous silicon can be contacted in the absence of a solvent. This procedure can be carried out at an elevated temperature, such as a temperature above about 50° C., or above about 100° C. Additionally, the non-solvent method can be carried out at an increased atmospheric pressure, such as about 2 to about 20 atmospheres, about 5 to about 10 atmospheres, or about 5 to about 20 atmospheres.

The acid used in the conversion of glycerol to 1,3-propanediol can be an inorganic acid, such as a mineral acid, for example, sulfuric acid, phosphoric acid, hydrochloric acid, or the like. Alternatively, the acid can be an organic acid, such as a sulfonic acid, such as phenyl sulfonic acid, or a carboxylic acid, for example, a ($C_1$-$C_3$)carboxylic acid. The ($C_1$-$C_3$) carboxylic acid can be acetic acid or an acetic acid derivative, for example, trifluoroacetic acid. The acid can be present in excess, in a equimolar amount, or in a sub-stoichiometric amount, with respect to the moles of glycerol. Typically, the acid is present in a catalytic amount, for example, about 5 mol % to about 50 mol %.

The reaction can provide suitable amounts of PDO in short periods of time, typically in less than one day. Finally, the method includes isolating the resulting 1,3-propanediol by a suitable method, including but not limited to distillation, chromatography, and derivatization.

Developing a system to make high value chemicals such as 1,3-propanediol ("PDO") from the glycerin stream will add value for biodiesel producers who implement the new technology. PDO is currently produced mainly from fossil-based resources and by costly chemical processes. The procedures described herein provide an economical method for preparing PDO and also provide a use for rejected and used silicon wafers from the semiconductor industry.

BRIEF DESCRIPTION OF THE DRAWINGS

The following drawings form part of the present specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

DETAILED DESCRIPTION

The current price per pound of glycerin in its impure form ranges near 15 cents, while the price for a pound of polytrimethylene terephthalate ("PTT") as manufactured from 1,3-propanediol ("PDO") is nearly seven dollars. Numerous PDO consumers exist and are presently using either poisonous and polluting fossil-fuel manufacturing processes, or slow and costly starch fermentation processes. Thus, a novel and commercially economic pathway to supplying PDO, a major commodity chemical, from renewable sources is desired.

The invention provides an alternate means of manufacturing PDO from glycerin, for example, from a lipid-derived glycerin obtained as a by-product of the biodiesel industry. The method can employ ionic hydrogenation, for example, with an acid and porous silicon, to provide the PDO. Ionic hydrogenation is a selective deoxygenation reaction that uses the combination of a silane and an acid to convert a secondary alcohol into a methylene (—$CH_2$—) group. The silane can be derived from electrochemically etched silicon wafers. These wafers can be obtained from rejected and/or used silicon chips.

PDO is a high value chemical intermediate used in resins, engine coolants, dry-set mortars, water-based inks, and especially in the manufacture of PTT. PPT polymers are marketed under trademarks such as Dupont's Sorona®, CDP Natureworks®, and Shell Chemical's Corterra™.

Other products can be improved by the use of PDO. These include dry-set mortars such as Portland cement that are modified with PDO. These mortars are better able to retain moisture while curing and they become stronger bonding agents when modified with PDO. Polymers based on PDO exhibit lower melting points, improved dye characteristics, and better fiber resiliency and stretch recovery. These improved characteristics are not obtained when ethylene glycol is used in place of PDO. PTT, such as the product recently developed by Shell Chemical, exhibits the elastic recovery of nylon and the chemical resistance of polyester, which are important properties for commercial polymers.

The invention provides a method to prepare 1,3-propanediol by contacting glycerol with porous silicon in the presence of an acid, wherein the porous silicon contains an effective amount of silicon hydride moieties. Porous silicon is a nano- or microporous crystalline silicon material, whose surface contains many of the same functional groups as organosilanes. Porous silicon can be easily produced by electrochemical etching processes.

Figure 2:
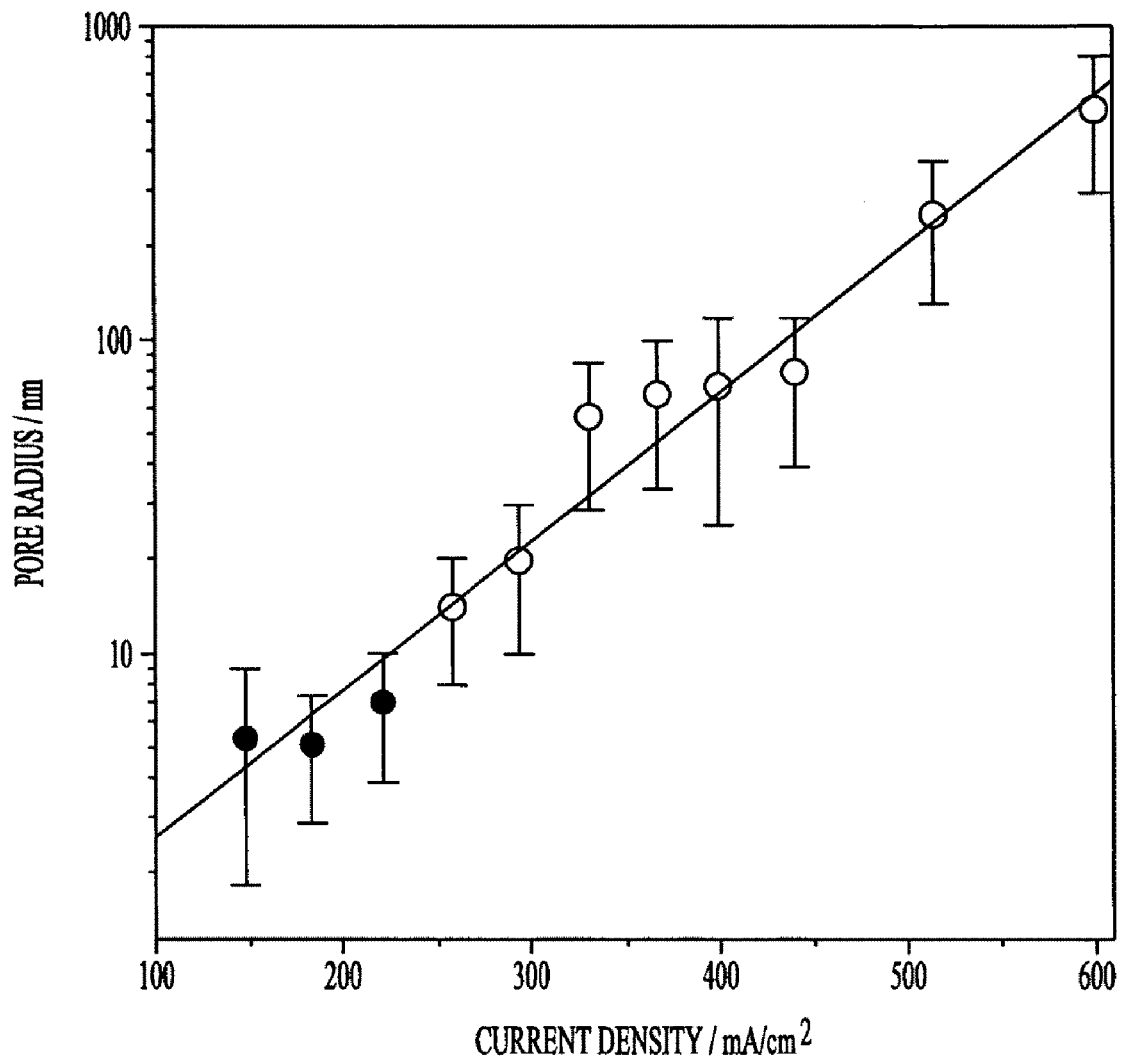
FIG. 2 illustrates a plot of the logarithm of the measured pore radii versus the electrochemical etching current density in one representative experiment. This figure shows that the pore radii of PSi can be regulated by the etching current density.

The pore diameter, pore geometric shape, and surface property of porous silicon can easily be modulated. As shown in FIG. 2, the pore radii can be controlled by the etching density. The etching time also can affect the thickness of the PSi layer. The typical thickness for our etching process is around 200 microns. By using porous silicon as a reductant, it is possible to selectively reduce glycerol without protecting the primary hydroxyl groups of glycerol, due to the natural stability of the carbocation intermediate. The pore size and surface modification (e.g., the HF etching) of porous silicon provides selectivity among the alcohol groups of the glycerol.

The invention provides a process that overcomes many of the disadvantages of known glycerol reduction processes. Porous silicon is easy to prepare and environmentally friendly. The only byproduct generated from the porous silicon-induced glycerol reduction is silica, which does not cause environmental concerns. By using a Lewis acid as co-reagent, glycerol can be selectively reduced without protection of the primary alcohol functional groups. Furthermore, the surface silicon hydride groups can be regenerated, which allows reuse of the porous silicon catalyst or reagent.

Current research involving porous silicon is focused toward applying porous silicon to sensors and optical and electronic properties, not toward its use as a heterogeneous reducing agent. Synthetic organic chemists interested in such reductions typically focus on developing homogeneous reductants.

Ionic hydrogenation is a seldom-studied deoxygenation reaction that involves the combination of a silane and an acid (e.g. trifluoroacetic acid) to convert a secondary alcohol into a methylene group. The reaction proceeds by way of a carbocation intermediate. It is described herein how a porous silicon ("PSi") material has now been demonstrated as an economical reagent to convert glycerin into 1,3-propanediol.

The ionic hydrogenation reaction for the preparation of 1,3-propanediol is shown below in Scheme 1. The reduction of glycerol using an activated PSi as described herein can provide 1,3-propanediol in approximately 55% yield.

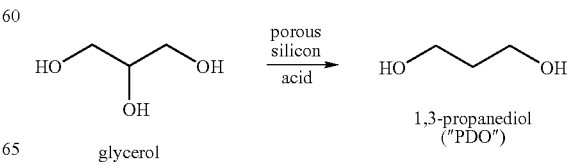

Scheme 1.

The acid component is catalytic and only 5 mole percent provides suitable conversion of the glycerol.

Figure 1:
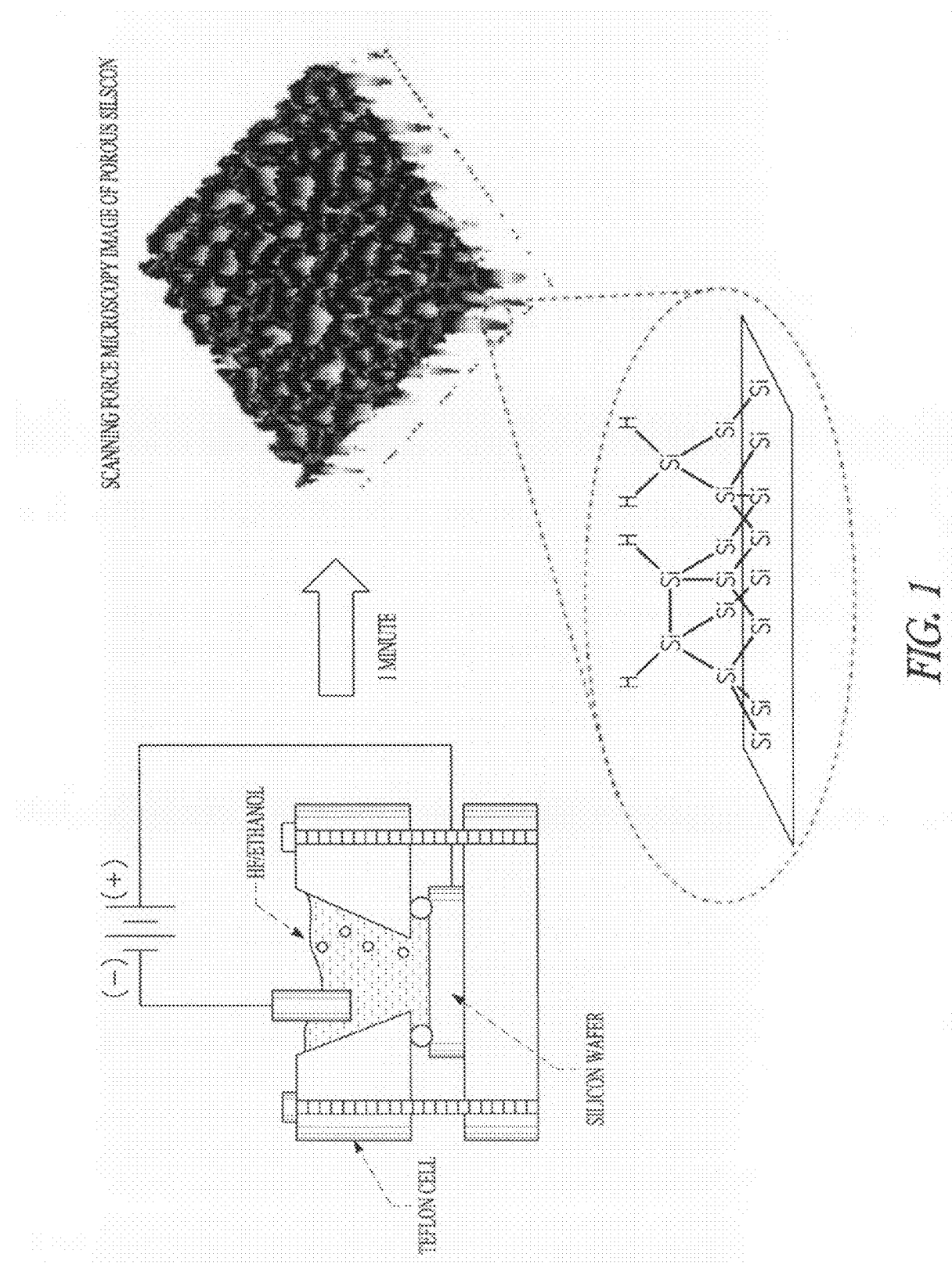
FIG. 1 illustrates a schematic of a process for electrochemically etching a silicon wafer; in less than 1 minute the procedure provides a silicon hydride-terminated PSi material composed of three types of silicon hydride groups, Si—$H_x$ (where x=1, 2 or 3) as identified by characteristic IR absorbances.

Additionally, a process was developed for electrochemically etching various silicon wafers. The process generates a variety of porous silicon (PSi) materials with high surface area (400-600 m$^2$/g) and tunable pore diameter (1-1000 nm). In a typical procedure (see, e.g., FIG. 1), a silicon wafer is electrochemically etched in less than 1 minute to yield a silicon hydride-terminated PSi material composed of three types of silicon hydride groups, Si—H$_x$ (wherein x=1, 2 or 3) as identified by characteristic IR absorbances.

These PSi materials are capable of converting glycerol to PDO under mild reaction conditions in a 55% yield. After the reaction, the PSi material was recycled and reused until it became fully oxidized SiO$_2$ ("silica", or "sand"). Because the PSi material can be easily generated from waste silicon wafers, this approach could be used for the selective reduction of glycerin in an economical and environmentally friendly manner.

The reactivity of the PSi can be fine-tuned and optimized by varying the pore diameter of the nanoporous silicon hydride materials. By varying pore diameters, the mass transport properties of the conversion of glycerin to 1,3-propanediol can be regulated. It was discovered that the pore radius of PSi is exponentially dependent on the current density applied during the electrochemical etching process as shown in FIG. 2. By increasing the current density, a series of PSi materials with various pore diameters ranging from 1 nm to 1 micron was prepared.

The rates of the ionic hydrogenation reaction of glycerin with the different PSi materials to yield 1,3-propanediol was investigated. It was envisioned that the PSi materials with large pore diameters would allow fast mass-transport of the reactant and the product into and out of the nanopores, thereby offer rapid kinetic profiles. The reaction kinetics of the PSi with large pore size (radius >200 nm) has been found to be significantly faster (by a factor of 5) than those of smaller pores.

The reduction process requires the presence of an acid and a Si—H (silicon hydride) functionality. This functionality is supplied on the pore surfaces of the PSi material. Because reduction of the secondary hydroxyl group on glycerol can in principle be achieved with either weak or strong acids, the process was examined using a variety of acids such as acetic acid, chloroacetic acid, and sulfuric acid.

The reduction can be carried out at room temperature (~23° C.), or at an elevated temperature (reflux temperature of a suitable solvent system). Solvents with boiling points from about 30° C. to about 115° C. are suitable for the reduction reaction, such as methylene chloride, chloroform, and toluene. Gram-scale experiments indicate that the reduction of glycerol can be conducted without a solvent at about 80° C. The yield of isolated PDO was approximately 35-55%.

The PSi material derived from electrochemically etched silicon wafers can be obtained by recycling rejected and/or used silicon chips. These silicon chips exist in large quantities in the electronics and semiconductor industry and are currently handled as waste.

The following Examples are intended to illustrate the above invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

Some general techniques known to those of skill in the art have been described by Kursanov and coworkers (Kursanov et al., "Applications of Ionic Hydrogenation to Organic Synthesis", *Synthesis* 1974, (9), 633-51), and in other documents cited herein.

Example 1

Preparation of Hydride-Terminated Porous Silicon ("PSi")

Billions of single crystal silicon wafers are currently being manufactured around the world for various microelectronic applications. New wafers with a diameter of 30 cm cost approximately $400 each. They are produced from pure, single-crystal silicon, precision-engineered to a uniform thickness. Such precision is necessary to accommodate miniature electronic devices on the wafers, such as computer memory chips and processors. However, state-of-the-art manufacturing of the wafers is complex.

Currently, less than 50% of the processed silicon wafers actually end up as usable chips. Only 8% of the processed silicon wafers qualify for development work, and the rest are rejected. In addition, many existing microchips from various disposable electronic appliances are not recycled. They are typically treated as industrial waste due to the precise technical requirements demanded by the industry and the associated technical difficulties of reusing the used wafers. With such large waste streams, it is important to find alternative applications for the rejected and used silicon wafers to lower the cost and the rapidly increasing demand of microchip production.

Currently, the average price for test-grade silicon wafers is around $500 for 100 four-inch diameter wafers. This compares with typically $2,000 for 100 prime wafers from a new wafer manufacturer. Rejected silicon wafers are at least one order of magnitude cheaper than the test wafers, which would bring the price for the rejected wafers down to $50 for 100 four-inch diameter wafers.

Based on experimental results, 1 four-inch, test-grade, silicon wafer can be used to convert 1 liter (¼ gallon) of glycerol to approximately 780 grams of PDO. The cost of the electrochemical etching process (costs for the HF/ethanol solution, electricity, and the fabrication of the Teflon vessel) for one four-inch wafer is around twelve cents. Thus, the total cost for producing 1 kilogram of PDO is approximately 85 cents by using commercially available "rejected" silicon wafers.

Based on a recent economic analysis on the cost of production for PDO (http://www.sriconsulting.com/PEP/Reports/Phase_2003/RW2003-10/RW2003-10.html), Shell Chemical can produce 1 kilogram of PDO for $1.83. By comparing the cost associated with the methods disclosed herein with that of the Shell technology, it is believed that the methods described herein are highly economical. Furthermore, glycerol is used as the feedstock, which is a byproduct of the biodiesel synthesis, further establishing the economic value of the process.

Accordingly, p-typed silicon wafers (B-doped, (100) orientation) with resistivity in the range of 0.6-1.0 mΩ cm (p$^{++}$) were used for fabrication of porous silicon. These p-type silicon wafers were rinsed thoroughly with pure ethanol, and dried under a stream of nitrogen. The silicon wafers were then subjected to anodic etching in ethanolic HF solution. Cleaned silicon wafers were placed in Teflon etching cells, which were in contact with strips of aluminum foil. Platinum mesh served as counter electrodes to provide homogeneous electrical fields.

The p$^{++}$ wafers were etched in HF/EtOH 3:1 (v/v) in the dark by a galvanometer with current density around 200±50 mA/cm$^2$ for 2 minutes. After etching, the sample was rinsed thoroughly with ethanol and methylene chloride, and then dried under vacuum prior to use. Successful porous silicon fabrication is realized upon the appearance of a green color in the reaction mixture, observed after anodization. The reaction can be further monitored by observing an increase in the characteristic Si—H peaks (vibrational bands at 2110 cm$^{-1}$) in an FT-IR spectrum.

Example 2

General procedure for Polyol Ionic Reduction by Porous Silicon

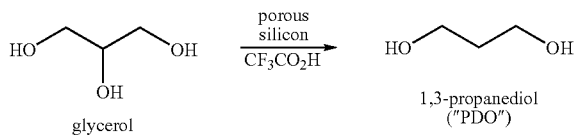

A solution of glycerol (11.2 mmol) in 20 mL CH$_2$Cl$_2$ was charged with a freshly prepared porous silicon chip (Example 1). Trifluoroacetic acid (TFA) (3.4 mL, 44.7 mmol) was added to the solution via syringe. The mixture was allowed to stir at ambient temperature (~23° C.) for 20 hours. The solvent was then removed under reduced atmospheric pressure. Column chromatography was used to separate the PDO from product impurities. The desired 1,3-propanediol product was isolated in 32-55% yield.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to prepare 1,3-propanediol comprising contacting glycerol with porous silicon in the presence of an acid, followed by isolating the resulting 1,3-propanediol, wherein the porous silicon contains silicon hydride moieties.

2. The method of claim 1 wherein the glycerol and the porous silicon are contacted in the presence of a solvent.

3. The method of claim 2 wherein the solvent is an organic solvent.

4. The method of claim 3 wherein the organic solvent is a chlorinated organic solvent.

5. The method of claim 4 wherein the chlorinated organic solvent is methylene chloride.

6. The method of claim 1 wherein the glycerol and the porous silicon are contacted in the absence of a solvent, at a temperature above about 50° C.

7. The method of claim 1 wherein the porous silicon comprises at least one of three types of silicon hydride moieties, wherein the silicon hydride moieties comprise Si—H$_x$, wherein x is 1, 2 or 3.

8. The method of claim 1 wherein the porous silicon has radii of about 1 nm to about 500 nm.

9. The method of claim 1 wherein the porous silicon has a surface area of about 200 to about 800 m$^2$/g.

10. The method of claim 1 wherein the porous silicon has a surface area of about 400 to about 600 m$^2$/g.

11. The method of claim 1 wherein the acid is an organic acid.

12. The method of claim 11 wherein the organic acid is a (C$_1$-C$_3$)carboxylic acid.

13. The method of claim 12 wherein the (C$_1$-C$_3$)carboxylic acid is an acetic acid derivative.

14. The method of claim 13 wherein the acetic acid derivative is trifluoroacetic acid.

15. The method of claim 1 wherein the acid is present in a sub-stoichiometric amount, with respect to the moles of glycerol.

* * * * *